(12) United States Patent
Flashner-Barak et al.

(10) Patent No.: US 6,476,006 B2
(45) Date of Patent: Nov. 5, 2002

(54) COMPOSITION AND DOSAGE FORM FOR DELAYED GASTRIC RELEASE OF ALENDRONATE AND/OR OTHER BIS-PHOSPHONATES

(75) Inventors: Moshe Flashner-Barak, Petach Tikva (IL); Vered Rosenberger, Jerusalem (IL); Mazal Dahan, Jerusalem (IL); Yitzhak Lerner, Petach Tikva (IL)

(73) Assignee: Teva Pharmaceutical Industries, Ltd., Petah Tiqva (IL)

(*) Notice: Subject to any disclaimer, the term of this patent is extended or adjusted under 35 U.S.C. 154(b) by 0 days.

(21) Appl. No.: 09/770,898

(22) Filed: Jan. 26, 2001

(65) Prior Publication Data

US 2002/0015733 A1 Feb. 7, 2002

Related U.S. Application Data

(60) Provisional application No. 60/260,438, filed on Jan. 9, 2001, and provisional application No. 60/213,832, filed on Jun. 23, 2000.

(51) Int. Cl.[7] .......................... A01N 57/26; A61K 31/66
(52) U.S. Cl. .......................... 514/76; 514/102; 514/106; 514/109
(58) Field of Search .................. 424/484; 514/102, 514/106, 109, 76

(56) References Cited

U.S. PATENT DOCUMENTS

| | | | |
|---|---|---|---|
| 2,996,431 A | 8/1961 | Barry | |
| 3,139,383 A | 6/1964 | Neville | |
| 3,995,058 A | 11/1976 | Hammond et al. | |
| 4,140,755 A | 2/1979 | Sheth et al. | |
| 4,167,558 A | 9/1979 | Sheth et al. | |
| 4,407,761 A | 10/1983 | Blum et al. | |
| 4,434,153 A | 2/1984 | Urquhart et al. | |
| 4,621,077 A | 11/1986 | Rosini et al. | |
| 4,704,285 A | 11/1987 | Alderman | |
| 4,705,651 A | 11/1987 | Staibano | |
| 4,721,613 A | 1/1988 | Urquhart et al. | |
| 4,752,470 A | 6/1988 | Mehta | |
| 4,756,911 A | 7/1988 | Drost et al. | |
| 4,758,436 A | 7/1988 | Caldwell et al. | |
| 4,764,380 A | 8/1988 | Urquhart et al. | |
| 4,767,627 A | 8/1988 | Caldwell et al. | |
| 4,853,229 A | 8/1989 | Theeuwes | |
| 4,922,007 A | 5/1990 | Kieczkowski et al. | |
| 4,983,398 A | 1/1991 | Gaylord et al. | |
| 5,007,790 A | 4/1991 | Shell | |
| 5,019,651 A | 5/1991 | Kieczykowski et al. | |
| 5,051,262 A | 9/1991 | Panoz et al. | |
| 5,198,229 A | 3/1993 | Wong et al. | |
| 5,356,887 A * | 10/1994 | Brenner et al. ............. 514/108 |
| 5,431,920 A * | 7/1995 | Bechard ...................... 424/480 |
| 5,648,491 A | 7/1997 | Dauer et al. | |
| 5,780,057 A | 7/1998 | Conte et al. | |
| 5,837,284 A | 11/1998 | Mehta et al. | |
| 5,840,756 A | 11/1998 | Cohen et al. | |
| 5,847,726 A | 12/1998 | Hori | |
| 6,120,803 A | 9/2000 | Wong et al. | |
| 6,121,253 A * | 9/2000 | Han et al. .................... 514/102 |
| 6,143,326 A | 11/2000 | Mockel et al. | |
| 6,207,197 B1 | 3/2001 | Illum et al. | |
| 6,261,601 B1 | 7/2001 | Talwar et al. | |
| 6,340,475 B2 | 1/2002 | Shell et al. | |

FOREIGN PATENT DOCUMENTS

| | | |
|---|---|---|
| EP | 0 761 209 | 3/1997 |
| GB | 2 118 042 A | 10/1983 |
| JP | H4-346919 | 12/1992 |
| WO | WO 96/39410 | 12/1996 |
| WO | WO 98/11879 | 3/1998 |
| WO | WO 99/04764 | 2/1999 |

OTHER PUBLICATIONS

US 6,034,101, 3/2000, Gupta et al. (withdrawn)
Hwang, Sung–Joo; Park, Haesun; Park, Kinam, "Gastric Retentive Drug–Delivery Systems", Critical Review in Therapeutic Drug Carrier Systems, 1998, vol. 15, Issue 3, pp. 243–284.
Chen, Jun; Park Kinam, "Synthesis and characterization of superporous hydrogel composites", Journal of Controlled Release 65, 2000, pp. 73–82.
The United States Pharmacopeia and The National Formulary, Jan. 1, 2000, 24/19, p. 2235 (1999).
Chen, Jun; Blevins, William E.; Park, Haesun; Park, Kinam, "Gastric retention properties of superporous hydrogel composites", Journal of Controlled Release 64, 2000, pp. 39–51.
M.I. Kabachnik, T. Ya. Medved, et al. "Synthesis and Acid–Base and Complexing Properties of Amino–Substituted α–Hydroxyalkylidenediphosphonic Acids," pp. 374–377.

* cited by examiner

*Primary Examiner*—Alton Pryor
(74) *Attorney, Agent, or Firm*—Kenyon & Kenyon

(57) ABSTRACT

The present invention provides compacted pharmaceutical composition for oral administration to a patient which expands upon contact with gastric fluid to retain a dosage form in the patient's stomach for an extended period of time, the formulation comprising a non-hydrated hydrogel, a superdisintegrant and tannic acid. The present invention further provides a pharmaceutical dosage form containing an active ingredient, and the compacted pharmaceutical composition. The invention further provides a dosage form suitable for delivering a therapeutic bis-phosphonate such as alendronate to the stomach of a patient over and extended period.

42 Claims, No Drawings

COMPOSITION AND DOSAGE FORM FOR DELAYED GASTRIC RELEASE OF ALENDRONATE AND/OR OTHER BIS-PHOSPHONATES

CROSS-REFERENCE TO RELATED APPLICATIONS

This application claims the benefit under 35 U.S.C. §119 (e) of U.S. provisional applications Ser. No. 60/213,832, filed Jun. 23, 2000 and Ser. No. 60/260,438, filed Jan. 9, 2001, the contents of which are incorporated herein by reference.

FIELD OF THE INVENTION

The present invention relates to gastric retention systems and to pharmaceutical dosage forms that use them to release a drug in a patient's stomach or duodenum. More particularly, the invention relates to gastric retention systems suitable for use with bis-phosphonates such as alendronic acid and its pharmaceutically acceptable salts and hydrates thereof, to release these drugs in a controlled manner.

BACKGROUND OF THE INVENTION

After discovery of a new drug for treatment of a human disease further investigation must be undertaken to determine whether it is most effective to administer the drug to a patient intravenously, transdermally, subcutaneously or orally. Orally administered drugs are easy to administer and therefore are often favored whenever an oral route is feasible. However, compliance problems sometimes occur with orally administered drugs when the dosage form is inconvenient to take or must be taken frequently or at inconvenient times. Orally administered drugs are often presented to a patient in such dosage forms as tablets, pills, lozenges and capsules. Most orally administered drugs are absorbed into the bloodstream from the patient's gastrointestinal tract, excepting inhalants which are absorbed by the lungs and sinuses.

Orally-administered drug may be absorbed more readily by the gastrointestinal ("GI") tract through either the stomach wall or the intestine wall. Few drugs are efficiently absorbed by the colon. Tablets that are designed to carry drugs that are more readily absorbed through the intestine wall are sometimes covered with a coating that is resistant to the acidic conditions of the stomach but which decomposes under the basic conditions of the intestine. This enteric coating allows the tablet to transit the stomach without releasing the active ingredient until it reaches the portion of the GI tract where it is most readily absorbed. This enteric-coating strategy is also effective when the drug is caustic to the lining of the stomach or decomposes under acidic conditions.

It is sometimes desirable that a drug be released in a patient's stomach rather than in the intestine. One such instance is when it is therapeutically advantageous to release the drug over several hours. The average residence time of solid food in the small intestine is about three hours. A controlled release pharmaceutical dosage form may pass through the stomach and intestine and into the colon before the active ingredient has been completely released. However, if the dosage form is retained in the stomach, complete release occurs upstream of the small intestine and the active ingredient will enter the intestine in an unbound state in which it can be readily absorbed before reaching the colon.

It is also desirable to release a drug in the stomach when it is unstable to the basic conditions of the intestine. A composition that is formulated to dissolve upon contact with any aqueous solution will at least partially dissolve in the stomach because it reaches the stomach before it reaches the intestine. However, the average residence time of food in the stomach is only about 1 to 3 hours. Unless the drug is very rapidly absorbed, or the residence time is increased, some of the drug will pass to the intestine. An unstable drug will at least partially decompose to a product compound that either is not absorbed or, if absorbed, may not exert the desired therapeutic effect. Accordingly, decomposition of a base sensitive drug that passes into the intestine reduces the effectiveness of the dosage and, as well, introduces an uncontrollable factor that is detrimental to accurate dosing.

For the foregoing reasons, formulation chemists have developed strategies to increase the retention time of oral dosages in the stomach. One of the general strategies, involves using an intragastric expanding dosage form that swells upon contact with stomach juices, preventing its passage through the pylorus. Intragastric expanding dosage forms use hydrogels which expand upon contact with water to expand the dosage form to sufficient size to prevent its passage through the pylorus. An example of such a dosage form is described in U.S. Pat. No. 4,434,153. The '153 patent discloses a device for executing a therapeutic program after oral ingestion, the device having a matrix formed of a non-hydrated hydrogel and a plurality of tiny pills containing a drug dispersed throughout the matrix.

As reviewed by Hwang, S. et al. "Gastric Retentive Drug-Delivery Systems," *Critical Reviews in Therapeutic Drug Carrier Systems*, 1998, 15, 243–284, one of the major problems with intragastric expanding hydrogels is that it can take several hours for the hydrogel to become fully hydrated and to swell to sufficient size to obstruct passage through the pylorus. Since food remains in the stomach on average from about 1 to 3 hours, there is a high probability that known expanding dosage forms like that of the '153 patent will pass through the pylorus before attaining a sufficient size to obstruct passage.

The rate-limiting factor in the expansion of ordinary hydrogels is the rate of delivery of water to non-surfacial hydrogel material in the dosage form. Conventional non-hydrated hydrogels are not very porous when dry and ingress of water into the hydrogel is slowed further by the formation of a low permeability gelatinous layer on the surface after initial contact with water. One approach to solving this problem uses so-called superporous hydrogels. Superporous hydrogels have networks of pores of 100 μ diameter or more. Pores of that diameter are capable of efficient water transport by capillary action. Water reaches the non-surfacial hydrogel material quickly resulting in a rapid expansion of the superporous hydrogel to its full extent. However, there are also shortcomings attendant to the use of superporous hydrogels. They tend to be structurally weak and some are unable to withstand the mechanical stresses of the natural contractions that propel food out of the stomach and into the intestine. The superporous hydrogels tend to break up into particles too small to be retained.

Non-superporous hydrogels do not suffer from mechanical strength problems to as great an extent as superporous hydrogels. An additional advantage of using conventional hydrogels is that their degradation/erosion rates are well studied. The blended composition of the present invention should be compared with the superporous hydrogels described in Chen, J. and Park, K. *Journal of Controlled Release* 2000, 65, 73–82, wherein the mechanical strength of superporous hydrogels is improved by the polymerization of precursor hydrogel monomers in the presence of several superdisintegrants. The result of the polymerization described by Chen and Park is a new substance having interconnecting cross-linking networks of polyacrylate and, e.g. cross-linked carboxymethyl cellulose sodium. Such interconnecting networks are not expected to have the same degradation rates as conventional hydrogels made from the same precursor hydrogel monomers.

Many disease therapies can benefit from improvements in controlled gastric release technology, such as osteoporosis and Paget's disease. Bis-phosphonates such as alendronate, residronate, etidronate and teludronate are commonly prescribed drugs for treatment of these diseases. Despite their benefits, bis-phosphonates suffer from very poor oral bio-availability (Gert, B. J.; Holland, S. D.; Kline, W. F.; Matuszewski, B. K.; Freeman, A.; Quan, H.; Lasseter, K. C.; Mucklow, J. C.; Porras, A. G.; Studies of the oral bioavailablity of alendronate, *Clinical Pharmacology & Therapeutics* (1995) 58, 288–298), serious interference of absorption by foods and beverages other than water (ibid.), and side effects that consist of irritation of the upper gastrointestinal mucosa (Liberman, U. A.; Hirsch, L. J.; Esophagitis and alendronate, *N. Engl. J. Med.* (1996) 335, 1069–70) with the potential for this irritation leading to more serious conditions (*Physicians' Desk Reference,* Fosamax, Warnings).

To overcome these limitations, the bis-phosphonates, such as alendronate, are given in relatively large doses in a fasting condition while maintaining an upright position for at least a half an hour after dosing (*Physicians' Desk Reference,* Fosamax, Dosage and Administration). The standard treatment with the bis-phosphonates is chronic and daily, so the inconvenience to the patient can lead to non compliance with the dosage regimen. Since bis-phosphonates are not metabolized, dosing could be lowered to once a week instead of daily (70 mg per dose once a week in place of 10 mg per dose daily) by administering very large sustained-release doses of the drug, (Daifotis, A. G.; Santora II, A. C.; Yates, A. G.; Methods for inhibiting bone resorption, U.S. Pat. No. 5,994,329). While large dosing helps improve patient compliance, it has the potential of exacerbating the upper GI side effects of the drug.

Alendronate is best absorbed from the upper GI tract (duodenum and jejunum) (Lin, J. H.; Bisphosphonates: a review of their pharmacokinetic properties, *Bone* (1996), 18, 75–85. Porras, A. G.; Holland, S. D.; Gertz, B. J.; Pharmacokinetics of Alendronate, *Clin Pharmacokinet* (1999) 36, 315–328), and is better absorbed at a pH of ~6 (Gert, B. J.; Holland, S. D.; Kline, W. F.; Matuszewski, B. K.; Freeman, A.; Quan, H.; Lasseter, K. C.; Mucklow, J. C.; Porras, A. G.; Studies of the oral bioavailablity of alendronate, *Clinical Pharmacology & Therapeutics* (1995) 58, 288–298). Only gastric retention with controlled release allows for the extended delivery of a drug to the duodenum. Controlled release of the drug to the duodenum and jejunum parts of the intestine should allow an improvement in bioavailability, thus allowing a lowering of the total dose of the drug.

SUMMARY OF THE INVENTION

We have now found a rapidly expanding oral dosage form that swells rapidly in the gastric juices of a patient, thereby increasing the likelihood that an active ingredient carried by the form will be released in the stomach. This oral design form employs a blend of a superdisintegrant, tannic acid and one or more conventional hydrogels. The dosage forms of the present invention swell rapidly, yet because they do not require superporous hydrogels, do not have their associated mechanical strength problems.

The present invention further provides compacted pharmaceutical compositions for oral administration to a patient which expand upon contact with gastric fluid to retain a dosage form in the patient's stomach for an extended period of time, the formulation comprising a blend of a non-hydrated hydrogel, a superdisintegrant and tannic acid.

The present invention further provides a pharmaceutical dosage form containing an active ingredient and the compacted pharmaceutical composition.

Yet further, the present invention provides compositions and dosage forms for delayed release of bis-phosphonates. The dosage forms release the bis-phosphonates into the stomach of a patient suffering from osteoporosis or Paget's disease. The dosage forms include a drug delivery vehicle which retains the dosage form in the patient's stomach for an extended period of time. In some embodiments of the invention, the drug delivery vehicle further provides a means to slow the release of the bis-phosphonate. Bis-phosphonate is released into the stomach over at least a portion of the period that the dosage form is retained in the stomach.

DETAILED DESCRIPTION OF THE INVENTION

The present invention provides a carrier composition for a pharmaceutically active ingredient and dosage forms containing the carrier composition and the active ingredient. Tablets containing the inventive composition swell rapidly on contact with aqeuous solution, such as the gastric juices of a patient and simulated gastric fluid. Rapid swelling is achieved by a novel combination of hydrogel, superdisintegrant and tannic acid.

The preferred hydrogel of the present invention is hydroxypropylmethylcellulose, either alone or in combination with hydroxypropyl cellulose and/or a cross-linked acrylate polymer. Suitable cross-linked acrylate polymers include polyacrylic acid crosslinked with allyl sucrose commercially available under the trade name Carbopol® (BF Goodrich Chemical Ltd.) and polyacrylic acid cross linked with divinyl glycol. As further illustrated by Examples 5 and 8, below, a preferred hydrogel of the invention is a mixture of hydroxypropyl methylcellulose and hydroxypropyl cellulose. The most preferred hydrogel of the present invention is a combination of hydroxypropyl methylcellulose and hydroxypropyl cellulose in a weight ratio of from about 1:3 to about 5:3. The molecular weight of the hydrogels is not critical to practice of the invention.

The inventive composition also includes a superdisintegrant. Superdisintegrants are pharmaceutical excipients within a larger class of excipients known as disintegrants. Disintegrants are typically hydrophilic polymers of either natural or synthetic origin. Superdisintegrants are disintegrants that swell upon contact with water. Preferred superdisintegrants of the present invention swell to at least double their non-hydrated volume on contact with water. Exemplary of these superdisintegrants are cross-linked polyvinyl pyrollidone (a.k.a. crospovidone), cross-linked carboxymethyl cellulose sodium (a.k.a. croscarmelose sodium) and sodium starch glycolate. Crospovidone is commercially available from BASF Corp. under the tradename Kollidon® CL and from International Specialty Chemicals Corp. under the tradename Polyplasdone®. Croscarmellose sodium is commercially available from FMC Corp. under the tradename Ac-Di-Sol® and from Avebe Corp. under the tradename Primellose®. Sodium starch glycolate is commercially available from Penwest Pharmaceuticals Co. under the tradename Explotab® and from Avebe Corp. under the tradename Primojel®. The most preferred superdisintegrant is sodium starch glycolate.

The inventive composition further includes tannic acid. Tannic acid, also called tannin, gallotannin and gallotannic acid, is a naturally occurring constituent of the bark and fruit of many trees. The term "tannins" conventionally refers to two groups of compounds, "condensed tannins" and "hydrolyzable tannins." *Merck Index* monograph No. 8828 (9th ed. 1976). The hydrolyzable tannins are sugars that are esterified with one or more (polyhydroxylarene) formic acids. One common polyhydroxylarene formic acid is galloyl (i.e. 3,4, 5-trihydroxybenzoyl). Another common polyhydroxylarene formic acid substituent of tannins is meta-digallic acid. A common sugar moiety of tannins is glucose. The tannic acid of the present invention is selected from the hydrolyzable tannins, and especially glucose tannins in which one or more of the hydroxyl groups of glucose is esterified with gallic acid and/or meta-digallic acid.

The novel expanding composition of the present invention comprises hydroxypropyl methylcellulose, optionally in combination with other hydrogel polymers, a superdisintegrant and tannic acid. These excipients are preferably combined in a weight ratio, exclusive of any other excipients that may be present, of from about 20 wt. % to about 80 wt. % hydrogel, from about 10 wt. % to about 75 wt. % superdisintegrant and from about 2 wt. % to about 15 wt. % tannic acid. A preferred composition comprises from about 30 wt. % to about 55 wt. % superdisintegrant, about 5 wt. % (±2 wt. %) tannic acid, plus an amount of hydrogel sufficient to bring the total to 100 wt. %.

One especially preferred embodiment of the present invention is a rapidly expanding pharmaceutical composition comprising from about 10 wt. % to about 20 wt. % hydroxypropyl methyl cellulose, from about 45 wt. % to about 50 wt. % hydroxypropyl cellulose, about 25 wt. % to about 35 wt. % sodium starch glycolate and about 4 wt. % to about 6 wt. % tannic acid. A second especially preferred embodiment of the present invention is a rapidly expanding pharmaceutical composition comprising from about 20 wt. % to about 30 wt. % hydroxypropyl methyl cellulose, from about 10 wt. % to about 20 wt. % hydroxypropyl cellulose, about 45 wt. % to about 55 wt. % sodium starch glycolate and about 4 wt. % to about 6 wt. % tannic acid.

The novel composition of the invention can be prepared conventionally by dry blending. In order to form a structurally resilient mass upon contact with water or gastric fluid, the blended composition is compacted prior to hydration.

One object of the invention is to provide a dosage form such as a tablet that is retained in the stomach for an extended period of time by swelling to a size that prevents passage through the pylorus upon contact with gastric juices. Over time the swollen tablet degrades or erodes into particles that are sufficiently small to traverse the pylorus. The tablet may be compacted following conventional dry granulation or direct compression techniques.

The pharmaceutical dosage forms of the present invention comprise the compacted expanding composition of the invention and an active ingredient. Active ingredients that may be carried by these dosage forms include, but are in no way limited to, bis-phosphonates such as alendronic acid and its pharmaceutically acceptable salts and hydrates, levodopa, carbidopa, methylphenidate, diltiazem, irinotecan and etoposide. Preferably, the pharmaceutical dosage forms are retained in the stomach for three hours or more, more preferably about five hours or more. In order to obstruct passage through the pylorus, the dosage form preferably swells by a factor of five or more, more preferably about eight or more, within about fifteen minutes of contacting gastric fluid. Yet more preferably, such swelling is reached within about five minutes.

The novel composition of the invention can be prepared conventionally by dry blending. In order to form a structurally resilient mass upon contact with water or gastric fluid, the blended composition is compacted prior to hydration. The composition may be compacted following conventional dry granulation or direct compression techniques.

For instance, the blended composition may be compacted into a slug or a sheet and then comminuted into compacted granules. The compacted granules may be compressed subsequently into a final dosage form. It will be appreciated that the processes of slugging or roller compaction, followed by comminution and recompression render the hydrogel, superdisintegrant and tannic acid intragranular in the final dosage form. The active ingredient of the pharmaceutical may also be provided intragranularly by blending it with the expanding composition prior to compaction. Alternatively the active ingredient may be added after comminution of the compacted composition, which results in the active ingredient being extragranular.

As an alternative to dry granulation, the blended composition may be compressed directly into the final pharmaceutical dosage form using direct compression techniques. Direct compression produces a more uniform tablet without granules. Thus the active ingredient and any other desired excipients are blended with the composition prior to direct compression tableting. Such additional excipients that are particularly well suited to direct compression tableting include microcrystalline cellulose, spray dried lactose, dicalcium phosphate dihydrate and colloidal silica. An additional alternative to dry granulation is wet granulation. The blend of excipients may be granulated using water or an alcohol as a granulation solvent by standard granulation techniques known in the art followed by drying.

In addition to the above-described excipients, the rapidly expanding pharmaceutical composition and dosage form may further include any other excipients. One factor that must be taken into account in formulating a pharmaceutical composition is the mechanical process which the composition undergoes to be transformed into a dosage form, such as a tablet or capsule. Some excipients are added to facilitate this mechanical processing, such as glidants and tablet lubricants. Glidants improve the flow properties of the composition in powder or granule form while lubricants ease ejection of a tablet from the tableting dye in which it is formed by compression. Silicon dioxide is a common glidant, while magnesium is a common tablet lubricant. Thus, for example, the present inventive composition may further include silicon dioxide and magnesium stearate. Other excipients which may be mentioned are binders, that are added to prevent flaking and other types of physical disintegration of the tablet prior to ingestion by a patient. Yet other excipients are diluents whose presence causes the tablet to be larger and thus easier for a patient to handle.

Further increase in retention times can be realized by the addition of a compound that produces gas when contacted with acid, such as sodium bicarbonate. Sodium bicarbonate may be provided by blending into the expanding composition of the invention or may be an extragranular constituent of a tablet prepared by dry granulation. Sodium bicarbonate is preferably used at low concentration, of from about 0.5 wt. % to about 5 wt. % of expanding composition.

In addition to the above-described use of the expanding composition in tablets prepared by dry or wet granulation and compression, there are many other embodiments in which the expanding composition could be used to retain a drug delivery vehicle in the stomach. For instance, the expanding composition can be used to coat a smaller tablet (this is a preferred construction of a gastric retention dosage form of alendronate, described belo). The expanding composition can be used advantageously in this way in sustained delivery of a drug. After contact with aqueous fluid and swelling, the composition is highly porous. Thus, the release rate of a sustained release dosage form like a coated tablet or slowly desintegrating tablet is substantially unaffected by a coating of the expanding composition.

The expanding composition is also suited for the retention of drugs in the stomach when such drugs are contained in tablets that are either partially embedded in the expanding composition or attached thereto by an adhesive. These tablets can be of a slow release nature giving slow or controlled release for an extended period of time in the stomach. These tablets can further be of a delayed pulse release nature. The expanding composition of this invention will retain these forms in the stomach until the delay time has passed whereupon the drug will be released in a burst or pulse fashion. Attaching, or partially embedding, several such tablets, each timed with a different relay to release, to the composition of this invention, allows versatile dosing schemes from one taken dose. For example, one could deliver three (or more) timed doses in a pulse fashion while the patient needs to take the dose only once. The three doses would mimic taking three doses of the drug at the prescribed times, with the drug being absorbed from the stomach with each dose. Such dosing allows for improved compliance to dosage schedules and in many cases will lead thereby to improved therapy.

Delayed dosage forms that are not coupled to gastric retention will deliver each such dose in a different part of the GI tract with different absorption profiles for each of the doses. Such therapy would not be equivalent to taking three doses of the drug at the prescribed times, wherein the drug would have been absorbed from the stomach in each case.

The present invention provides a delayed release dosage form containing the delivery vehicle/composition of the invention and a therapeutic bis-phosphonate that is capable of delivering the bis-phosphonate to the stomach of a patient several hours after administration.

Suitable bis-phosphonates include alendronic acid and its pharmaceutically acceptable salts and hydrates thereof, as well as residronate, etidronate and teludronate.

The bis-phosphonate drug delivery vehicle may be formed from the afore-described hydrogel, superdisintegrant and tannic acid by blending or granulating. Regardless of the method by which the hydrogel, superdisintegrant and tannic acid are combined, they are preferably combined in a weight ratio, exclusive of the bis-phosphonate and any other excipients that may be present, of from about 50 wt. % to about 80 wt. % hydrogel, from about 10 wt. % to about 30 wt. % superdisintegrant and from about 5 wt. % to about 15 wt. % tannic acid. A yet more preferred drug delivery vehicle comprises from about 15 wt. % to about 25 wt. % superdisintegrant, about 10 wt. % (±2 wt. %) tannic acid, plus an amount of hydrogel sufficient to bring the total to 100 wt. %. One especially preferred bis-phosphonate delivery vehicle comprises from about 15 wt. % to about 20 wt. % hydroxypropyl methyl cellulose, from about 45 wt. % to about 55 wt. % hydroxypropyl cellulose, about 20 wt. % to about 25 wt. % carboxy methyl cellulose sodium and about 8 wt. % to about 12 wt. % tannic acid.

Dosage forms containing the drug delivery vehicle and bis-phosphonate swell rapidly on contact with aqueous solution, e.g. water, gastric fluid and acidic solutions like simulated gastric fluid. In order to obstruct passage through the pylorus, the drug delivery vehicle preferably swells by a factor of five or more, more preferably about eight or more, within about fifteen minutes of contacting gastric fluid. Yet more preferably, such swelling is reached within about five minutes. Preferably, the swelling causes retention of the pharmaceutical dosage forms in the stomach for three hours or more, more preferably about four hours or more, after which time the drug delivery vehicle either dissolves or degrades into fragments small enough to pass through the pylorus.

The invention further relates to specific pharmaceutical dosage forms containing a therapeutic bis-phosphonate and the drug delivery vehicle. These forms may have (a) a monolithic construction, such as a tablet made by conventional direct compression or granulation techniques wherein the active is dispersed in the drug delivery vehicle, (b) a layered construction wherein the active, alone or in mixture with any other excipients, form a layer that is bonded, e.g. by compression, to another layer formed of the drug delivery vehicle, (c) an encapsulated construction wherein either of the (a) or (b) type constructions are encapsulated, (d) a coated construction wherein a core containing the actives is coated with the drug delivery vehicle, and (e) a construction whereby the drug is incorporated in an optionally coated matrix tablet, said tablet being partially embedded in the drug delivery vehicle, or attached externally to the drug delivery vehicle by an adhesive.

A monolithic dosage form can be prepared by the direct compression and granulation methods previously described. The monolithic dosage form may be made in any shape desired, but it has been found that an ovoid or elliptical shape is advantageous for retaining the dosage form in the stomach. An ovoid or elliptical dosage form preferably is sized at between about 4 mm and 8 mm in two dimensions and between about 10 mm and 20 mm in the third dimension, more preferably about 6×6×16 mm. Monolithic dosage forms slow the release of the actives due to the diffusional barrier created by the surrounding swelled hydrogel. The diffusion may slow to the point that release occurs by erosion of the drug delivery vehicle.

In a monolithic dosage form, delayed release of the actives may be provided by coating the actives with a delay release coating according to methods known to the art. Thus, where the foregoing description of the present invention has described mixing, blending, granulating, compressing, etc. of the actives, it will be appreciated by those skilled in the art that the actives may previously be coated with a coating that erodes slowly in gastric fluid to provide a delay in release of the actives. In particular, a monolithic dosage form may contain microgranules, microcapsules or coated beads containing the actives.

A particularly preferred bis-phosphonate dosage form is a coated construction wherein the drug delivery vehicle coats a core containing the active. This construction is illustrated in detail with Examples 9–12, below. A coated construction delays the release of the active by providing a diffusional barrier through which the active must pass before it is released. As illustrated in the Examples, a coated construction can provide either a delayed/rapid release or a delayed/extended release of the active depending upon the formulation of the core.

A preferred layered construction is one which contains the drug delivery vehicle in one layer and the actives in another layer. Preferred dimensions for this embodiment are about 14×8 mm. A layered construction may be prepared by conventional multilayer compression techniques. A layered dosage form comprising two layers, one comprising the drug delivery vehicle and the other comprising the actives and any other desired excipients, may be made to delay release of the actives by coating only the actives-containing layer with a conventional coating resistant to gastric fluids. A further method of achieving a delay in the release is to formulate the drug containing layer as a matrix that delays diffusion and erosion or by incorporating the active substances in microcapsules or coated beads within the drug containing layer.

The drug delivery vehicle is also suited for the retention of the actives in the stomach when the actives are contained in tablets that are either partially embedded in the drug delivery vehicle or attached thereto by an adhesive. In addition to being of sustained release nature, these tablets can further be of a delayed pulse release nature or a delayed sustained release nature. The expanding composition of this invention will retain these forms in the stomach until the delay time has passed whereupon the drug will be released in a burst or pulse fashion or in a sustained fashion. Attaching, or partially embedding, several such tablets, each timed with a different delay to release, to the composition of this invention, allows versatile dosing schemes from one taken dose. For example, one could deliver three (or more) timed doses in a pulse fashion while the patient needs to take the dose only once. The three doses would mimic taking three doses of the drug at the prescribed times, with the drug being absorbed from the stomach with each dose. Such dosing allows for improved compliance to dosage schedules and in many cases will lead thereby to improved therapy. Delayed dosage forms that are not coupled to gastric retention will deliver each such dose in a different part of the GI tract with different absorption profiles for each of the doses. Such therapy would not be equivalent to taking three doses of the drug at the prescribed times, wherein the drug would have been absorbed from the stomach in each case.

In addition to the above-described dosage forms, there are many other dosage forms in which the drug delivery vehicle could be used to deliver a therapeutic bis-phosphonate over a sustained period in the stomach.

Having thus described the invention with reference to certain preferred embodiments, other embodiments will become apparent to one skilled in the art from consideration of the specification and examples. It is intended that the specification, including the examples, is considered exemplary only, with the scope and spirit of the invention being indicated by the claims which follow.

EXAMPLES

Examples 1–8

Materials

The HPMC used was HPMC K-15PM. The hydroxypropyl cellulose used was Klucel® HF NF, available from Hercules. The sodium croscarmellose used was Ac-Di-Sol® obtained from Avebe Corp. The crosslinked polyacrylic acid was Carbopol® 974P obtained from B.F. Goodrich Chemical Ltd. All materials were of pharmaceutical grade.

Preparation of Tablets

The compositions of each of the tablets are summarized in Table 1. All the compositions contain hydroxypropyl methyl cellulose, tannic acid, a superdisintegrant and 1% magnesium stearate. All of the excipients, except for magnesium stearate, were mixed simultaneously and thoroughly blended by hand. Magnesium stearate was then added at a level of 1% w/w and the blend was further mixed by hand until the magnesium stearate was uniformly distributed throughout the composition. The amount of each composition needed to produce a 5 mm thick tablet was determined and then that amount was compressed into 5 mm thick tablets on a Manesty f3 single punch tableting machine with a 10 mm diameter punch and die. Tablets ranged in weight from 350–400 mg and each had a hardness within the range of 5–7 KP as tested in an Erweka hardness tester.

TABLE 1

| | Example No. (wt. %) | | | | | | | |
|---|---|---|---|---|---|---|---|---|
| Excipient | 1 | 2 | 3 | 4 | 5 | 6 | 7 | 8 |
| hydroxypropyl methylcellulose | 23.8 | 32.7 | 30.3 | 23.8 | 26.7 | 38.5 | 34.8 | 15.9 |
| Hydroxypropyl cellulose | 0.0 | 0.0 | 0.0 | 0.0 | 16.0 | 19.2 | 0.0 | 47.6 |
| cross-linked polyacrylic acid | 0 | 0.0 | 0.0 | 0.0 | 0.0 | 0.0 | 8.7 | 0.0 |
| Total Hydrogel | 23.8% | 32.7% | 30.3% | 23.8% | 42.7% | 57.7% | 43.5% | 63.5% |
| Sodium starch glycolate | 71.4 | 65.4 | 60.6 | 0.0 | 53.3 | 38.5 | 52.2 | 31.7 |
| Sodium Croscarmellose | 0.0 | 0.0 | 0.0 | 71.4 | 0.0 | 0.0 | 0.0 | 0.0 |
| Tannic Acid | 4.8 | 2.0 | 9.1 | 4.8 | 4.0 | 3.8 | 4.3 | 4.8 |
| | 100% | 100% | 100% | 100% | 100% | 100% | 100% | 100% |

Swelling tests

The tablets were added to 40 ml of 0.1M HCl contained in a 50 ml beaker and maintained at 37±2° C. The tablets were removed after fifteen minutes with a tweezers and measured with a caliper. Gel strength was assessed qualitatively with the tweezers.

Results

The results of the swelling tests are summarized in Table 2. Swelling of the hydrogel was enhanced using either sodium croscarmellose or sodium starch glycolate. The formulation can optionally and advantageously contain a mixture of two hydrogel polymers demonstrated by the incorporation hydroxypropyl cellulose and carbopol in the formulations of Examples 5, 6 and 8. The tablet that expanded the most (36 times in volume) contained tannic acid at 5% with sodium croscarmellose as the disintegrant. The tablet with the second highest expansion (18×) also contained tannic acid at 5% but used sodium starch glycolate. Both of those gels were qualitatively weak compared to those of examples 5–8. The best performing tablets in terms of a high degree of expansion and good mechanical strength are those of Examples 5 and 8, which contained tannic acid at 5 wt. %, used both hydroxypropyl methylcellulose and hydroxypropyl cellulose hydrogel polymers and contained sodium starch glycollate as disintegrant.

TABLE 2

| Example No. | Degree of Swelling[a] | Strength |
| --- | --- | --- |
| 1 | 18.1 | moderate |
| 2 | 12.7 | moderate |
| 3 | 7.2 | moderate |
| 4 | 36 | moderate |
| 5 | 10.4 | strong |
| 6 | 2 | strong |
| 7 | 4.5 | strong |
| 8 | 9.7 | strong |

[a]ratio of hydrated tablet volume to dry tablet volume

Example 9

Sodium alendronate monohydrate was formulated into an immediate release tablet of 5-mm diameter with the composition of Table 3 by mixing the powders and direct compression in a standard rotary tablet press. Tablet hardness was between 7 and 12 kP.

TABLE 3

| Component | Weight (mg) |
| --- | --- |
| Sodium alendronate monohydrate | 11.6 mg[a] |
| Microcrystalline cellulose | 30 mg |
| Lactose for direct compression | 20 mg |
| Magnesium stearate | 0.5 mg |

[a]equivalent to 10 mg alendronic acid

This tablet was embedded into 800 mg of gastric retention delivery system (GRDS) matrix of formulation of Table 4 formed by dry mixing of the components and compression in a Kilian RUD-20 press coat machine. The outer tablet is of oval shape with dimensions approximately 17×7×9 mm.

TABLE 4

| GRDS Component | weight % |
| --- | --- |
| HPMC (Methocel ® K-15M) | 17 |
| Tannic acid | 10 |
| HPC (Klucel ® HF) | 50 |
| Crosscarmelose (aci-di-sol ®) | 22 |
| Magnesium stearate | 1 |

The tablet was tested in a USP apparatus 2 dissolution tester at 37° C. in 500 ml 0.1N HCl to simulate gastric conditions. The tablet expanded in about 15 minutes to dimensions of 22×10×23 mm, large enough to effect gastric retention since the tablet in its swollen state will not fit through the pylorus. The results of the release of the alendronate are given in Table 5. Essentially no alendronate was released during the first three hours. The drug was then released at a relatively fast rate from the disintegrating inner tablet through the GRDS matrix.

TABLE 5

| Time (h) | Cumulative % release |
| --- | --- |
| 0 | 0 |
| 1 | 0 |
| 2 | 0 |
| 3 | 3 |
| 4 | 50 |
| 5 | 100 |

Example 10

Sodium alendronate monohydrate was formulated into an extended release tablet of 5-mm diameter with a composition shown in Table 6 by mixing the powders and direct compression in a standard rotary tablet press. Tablet hardness was between 7 and 12 kP.

TABLE 6

| Component | Weight (mg) |
| --- | --- |
| Sodium alendronate monohydrate | 11.6 mg[a] |
| Microcrystalline cellulose | 25 mg |
| Lactose | 25 mg |
| Magnesium stearate | 0.5 mg |

[a]equivalent to 10 mg alendronic acid

This tablet was embedded into 800 mg of Gastric Retention Delivery System (GRDS) matrix of formulation of Table 7 formed by dry mixing of the components and compression in a Kilian RUD-20 press coat machine. The outer tablet is of oval shape with dimensions about 17×7×9 mm.

TABLE 7

| Component | weight % |
| --- | --- |
| HPMC (Methocel K-15M) | 17 |
| Tannic acid | 10 |
| HPC (Klucel HF) | 50 |
| Crosscarmelose (aci-di-sol) | 22 |
| Magnesium stearate | 1 |

The tablet was tested in a USP apparatus 2 dissolution tester at 37° C. in 500 ml 0.1N HCl to simulate gastric conditions. The tablet expanded in 15 minutes to dimensions of 22×10×23 mm, sufficiently large to cause gastric retention. The results of the release of the alendronate are given in Table 8. Essentially no alendronate was released during the first three hours. The drug was then released at a slow extended release profile.

TABLE 8

| Time (h) | Cumulative % release |
| --- | --- |
| 0 | 0 |
| 1 | 0 |
| 2 | 0 |
| 3 | 2 |
| 4 | 9 |
| 5 | 15 |
| 6 | 21 |
| 7 | 27 |
| 8 | 32 |
| 9 | 36 |

Example 11

Sodium alendronate monohydrate (11.6 mg) was formulated into a tablet of 5-mm diameter with 50 mg of the GRDS composition shown in Table 7 above by mixing the powders and direct compression in a standard rotary tablet press. Tablet hardness was between 7 and 12 kP. This tablet is embedded into 800 mg of Gastric Retention Delivery System (GRDS) matrix formulation of Table X formed by dry mixing of the components and compression in a Kilian RUD-20 press coat machine. The outer tablet was of oval shape with dimensions about 17×7×9 mm.

The tablets were tested in a USP apparatus 2 dissolution tester at 37° C. in 500 ml 0.1N HCl to simulate gastric conditions. The tablet expand in about 15 minutes to dimensions of 22×10×23 mm, large enough to effect gastric retention. The results of the release of the alendronate are given in Table 9.

Essentially no alendronate was released during the first three hours. The drug was then released at a relatively constant pace from the inner tablet through the GRDS matrix.

TABLE 9

| Time (h) | Cumulative % release |
|---|---|
| 0 | 0 |
| 1 | 0 |
| 2 | 0 |
| 3 | 5 |
| 4 | 15 |
| 5 | 30 |
| 6 | 50 |
| 7 | 65 |
| 8 | 75 |
| 9 | 80 |
| 12 | 100 |

Example 12

Sodium alendronate monohydrate was granulated with 0.5% HPC (Klucel HF) in ethanol. The granulate was dried and milled to a free flowing powder. This granulate was mixed with the GRDS matrix formulation of Table 7 in a ratio of 11.8 mg alendronate granulate to 850 mg GRDS matrix such that the alendronate matrix was dispersed homogeneously in the matrix. Tablets were pressed in a standard rotary press using oval tooling to give tablets with an approximate size of 17×7×8 mm. 500 grams of these tablets were coated in a perforated pan coater with 5% HPMC suspended in ethanol under the following conditions to give tablets with a coating level of 15% w/w.

| Coating conditions: | |
|---|---|
| Bed temperature: | 40° C. |
| Solution flow rate: | 7.5 ml/min |
| Coating time: | about 20 minutes |

The tablets were tested in a USP apparatus 2 dissolution tester at 37° C. in 500 ml 0.1N HCl to simulate gastric conditions. The tablet expands quickly, but slower than in the previous examples (in about 45 minutes) to dimensions of 20×8×20 mm which is large enough to effect gastric retention. The results of the release of the alendronate are given in Table 10. A low level of alendronate was released during the first three hours. The drug was then released at a relatively constant pace from the GRDS matrix.

TABLE 10

| Time (h) | Cumulative % release |
|---|---|
| 0 | 0 |
| 1 | 1 |
| 2 | 3 |
| 3 | 5 |
| 4 | 25 |
| 5 | 45 |
| 6 | 65 |
| 7 | 85 |
| 8 | 100 |

Example 13

Tablets from example 11 were administered to 3 beagle dogs in a crossover design versus an immediate release alendronate formulation. Urine samples were collected for 48 hours and an overall AUC for alendronate was determined. The average bioavailability of the alendronate from the immediate release formulation was calculated to be ~1.5% while the bioavailablity of the gastric retention alendronate was found to be greater than 3%

We claim:

1. A pharmaceutical dosage form for oral administration to a patient which provides delayed gastric release of a therapeutically effective amount of a therapeutic bis-phosphonate, the dosage form comprising the bis-phosphonate and a drug delivery vehicle comprising a non-hydrated hydrogel, a superdisintegrant and tannic acid wherein upon contact with gastric fluid or simulated gastric fluid the non-hydrated hydrogel hydrates and the delivery vehicle expands.

2. The pharmaceutical dosage form of claim 1 wherein the superdisintegrant swells to at least double its non-hydrated volume on contact with water.

3. The pharmaceutical dosage form of claim 1 wherein the tannic acid comprises from about 2 weight percent to about 15 weight percent of the drug delivery vehicle.

4. The pharmaceutical dosage form of claim 1 wherein the bis-phosphonate either is not released or is released at a low level for a period of two hours resulting in a cumulative release of about 5% or less.

5. The pharmaceutical dosage form of claim 1 wherein the bis-phosphonate either is not released or is released at a low level for a period of three hours resulting in a cumulative release of about 5% or less.

6. The pharmaceutical dosage form of claim 1 wherein essentially no bis-phosphonate is released for a period of two hours resulting in a cumulative release after three hours of about 5% or less.

7. The pharmaceutical dosage form of claim 1 wherein the bis-phosphonate is selected from the group consisting of alendronic acid and its pharmaceutically acceptable salts and hydrates thereof, residronate, etidronate and teludronate.

8. The pharmaceutical dosage form of claim 1 wherein the bis-phosphonate is alendronic acid or one of its pharmaceutically acceptable salts and hydrates thereof.

9. The pharmaceutical dosage form of claim 8 wherein the bis-phosphonate is monosodium alendronate monohydrate.

10. The pharmaceutical dosage form of claim 8 wherein the bis-phosphonate is monosodium alendronate trihydrate.

11. The pharmaceutical dosage form of claim 8 wherein the bis-phosphonate is alendronic acid.

12. The pharmaceutical dosage form of claim 1 wherein the hydrogel comprises hydroxypropyl methylcellulose.

13. The pharmaceutical dosage form of claim 12 wherein the hydrogel further comprises hydroxypropyl cellulose.

14. The pharmaceutical dosage form of claim 13 wherein the hydrogel comprises hydroxypropyl methylcellulose and hydroxypropyl cellulose in a weight ratio of from about 1:3 to about 5:3.

15. The pharmaceutical dosage form of claim 2 wherein the superdisintegrant is selected from the group consisting of cross-linked polyvinylpyrrolidone, cross-linked carboxymethyl cellulose sodium and sodium starch glycolate.

16. The pharmaceutical dosage form of claim 15 wherein the superdisintegrant is sodium starch glycolate.

17. The pharmaceutical dosage form of claim 15 wherein the superdisintegrant is cross-linked carboxymethyl cellulose sodium.

18. The pharmaceutical dosage form of claim 3 wherein tannic acid comprises from about 5 weight percent to about 15 weight percent of the drug delivery vehicle.

19. A method of treating bone disease in a human patient in need of such treatment by administering to the patient the pharmaceutical dosage form of claim 1.

20. The method of claim 19 wherein the bone disease is metastatic bone disease.

21. The method of claim 19 wherein the bone disease is osteoporosis.

22. The method of claim 19 wherein the bone disease is Paget's disease.

23. A method of inhibiting bone resorption in a human patient in need of such treatment by administering to the patient the pharmaceutical dosage form of claim 1.

24. A method of treating hypercalcemia in a human patient in need of such treatment by administering to the patient the pharmaceutical dosage form of claim 1.

25. A method of treating malignancy in bone of a human patient in need of such treatment by administering to the patient the pharmaceutical dosage form of claim 1.

26. The pharmaceutical dosage form of claim 1 wherein the drug delivery vehicle comprises of from about 50 wt. % to about 80 wt. % of a hydrogel, of from about 10 wt. % to about 30 wt. % of a superdisintegrant, and of from about 5 wt. % to about 10 wt. % tannic acid.

27. The pharmaceutical dosage form of claim 26 capable of being retained in the stomach of a human patient for a period of at least two hours.

28. The pharmaceutical dosage form of claim 26 capable of being retained in the stomach of a human patient for a period of at least three hours.

29. The pharmaceutical dosage form of claim 26 wherein the dosage form swells by a factor of five or more within about fifteen minutes of contacting aqueous solution.

30. The pharmaceutical dosage form of claim 29 wherein the dosage form swells by a factor of eight or more within about fifteen minutes of contacting aqueous solution.

31. The pharmaceutical dosage form of claim 29 wherein the dosage form swells by a factor of five or more within about five minutes of contacting aqueous solution.

32. The pharmaceutical dosage form of claim 26 further comprising a substance that emits gas upon contact with acid.

33. The pharmaceutical dosage form of claim 32 wherein the substance that emits gas upon contact with acid is sodium bicarbonate.

34. The pharmaceutical dosage form of claim 26 wherein the hydrogel comprises hydroxypropyl methylcellulose.

35. The pharmaceutical dosage form of claim 34 wherein the hydrogel further comprises hydroxypropyl cellulose.

36. The pharmaceutical dosage form of claim 35 wherein the hydrogel comprises hydroxypropyl methylcellulose and hydroxypropyl cellulose in a weight ratio of from about 1:3 to about 5:3.

37. The pharmaceutical dosage form of claim 26 wherein the superdisintegrant is selected form the group consisting of cross-linked polyvinylpyrrolidone, cross-linked carboxymethyl cellulose sodium and sodium starch glycolate.

38. A coated pharmaceutical dosage form comprising a core which contains a therapeutic bis-phosphonate and optionally other pharmaceutical excipients and a coating around the core, wherein the coating comprises a hydrogel, a superdisintegrant and tannic acid.

39. The coated pharmaceutical dosage form of claim 38 comprising from about 50 wt. % to about 80 wt. % of a hydrogel, from about 10 wt. % to about 30 wt. % of a superdisintegrant, and from about 5 wt. % to about 10 wt. % tannic acid.

40. A coated pharmaceutical dosage form having a core comprising about 18 wt. % sodium alendronate monohydrate, about 48 wt. % microcrystalline cellulose and about 32 wt. % lactose, the core having a coating thereon which comprises about 17 wt. % HPMC, about 10 wt. % tannic acid, about 50 wt. % HPC and about 22 wt. % crosslinked carboxymethyl cellulose sodium.

41. A coated pharmaceutical dosage form having a core comprising about 18 wt. % sodium alendronate monohydrate, about 41 wt. % microcrystalline cellulose and about 41 wt. % lactose, the core having a coating thereon which comprises about 17 wt. % HPMC, about 10 wt. % tannic acid, about 50 wt. % HPC and about 22 wt. % crosslinked carboxymethyl cellulose sodium.

42. A method of making the dosage form of claim 40 or 41 comprising the steps of mixing powdered sodium alendronate monohydrate, microcrystalline cellulose and lactose, tableting the mixed powders to make a core, dry mixing the HPMC, tannic acid, HPC and cross-linked carboxymethyl sodium to produce a coating mix, embedding the core in the coating mix and compacting the coating mix to produce the dosage form.

* * * * *